US008268337B2

(12) United States Patent
Wheeler

(10) Patent No.: US 8,268,337 B2
(45) Date of Patent: Sep. 18, 2012

(54) **NONTOXIC KILLER OF *E. COLI* AND OTHER PROBLEM MICROORGANISMS**

(76) Inventor: Jack A. Wheeler, Nashville, TN (US)

( * ) Notice: Subject to any disclaimer, the term of this patent is extended or adjusted under 35 U.S.C. 154(b) by 1226 days.

(21) Appl. No.: 11/129,216

(22) Filed: May 13, 2005

(65) Prior Publication Data

US 2005/0272820 A1    Dec. 8, 2005

Related U.S. Application Data

(60) Provisional application No. 60/571,303, filed on May 14, 2004, provisional application No. 60/573,396, filed on May 20, 2004.

(51) Int. Cl.
*A61K 9/08* (2006.01)
*A23L 3/34* (2006.01)
*A01N 33/12* (2006.01)

(52) U.S. Cl. .................. 424/405; 426/332; 514/643

(58) Field of Classification Search .............. 426/332
See application file for complete search history.

(56) References Cited

U.S. PATENT DOCUMENTS

| | | | |
|---|---|---|---|
| 4,022,911 A | 5/1977 | Goldhaft et al. |
| 4,852,216 A | 8/1989 | Clayton et al. |
| 5,364,650 A | 11/1994 | Guthery |
| 5,419,908 A | 5/1995 | Richter et al. |
| 5,604,250 A * | 2/1997 | Oppong et al. | 514/367 |
| 5,827,870 A * | 10/1998 | Chodosh | 514/390 |
| 5,900,266 A | 5/1999 | Iannotti et al. |
| 5,980,375 A | 11/1999 | Anderson et al. |
| 6,010,729 A | 1/2000 | Gutzmann et al. |
| 6,039,992 A | 3/2000 | Compadre et al. |
| 6,103,286 A | 8/2000 | Gutzmann et al. |
| 6,113,963 A | 9/2000 | Gutzmann et al. |
| 6,183,807 B1 | 2/2001 | Gutzmann et al. |
| 6,326,042 B1 | 12/2001 | Iannotti et al. |
| 6,525,071 B2 | 2/2003 | Dyer |
| 6,534,075 B1 | 3/2003 | Hei et al. |
| 6,545,047 B2 | 4/2003 | Gutzmann et al. |
| 2004/0186183 A1* | 9/2004 | Johnson | 514/643 |

FOREIGN PATENT DOCUMENTS

WO    WO 94/27436    12/1994

OTHER PUBLICATIONS

EPA Reregistration Eligibility Decision for Alkyl Dimethyl Benzyl Ammonium Chloride (ADBAC), Aug. 2006, pp. 1-9.*

* cited by examiner

*Primary Examiner* — Kortney L Klinkel
(74) *Attorney, Agent, or Firm* — Alston & Bird LLP

(57) ABSTRACT

The present invention provide a composition of non-toxic low-cost ingredients that effectively kill pathologic bacteria and methods for use of the composition. The present invention comprises novel compositions and methods for controlling enteric pathogens and spoilage organisms such as *Salmonella, Escherichia, Campylobacter, Listeria, Pseudomonas* and Enterobacteracae on the surface of meat products and food preparation surfaces.

46 Claims, 3 Drawing Sheets

Effect of Sanitizer on *Listeria monocytogenes*

NONTOXIC KILLER OF *E. COLI* AND OTHER PROBLEM MICROORGANISMS

CROSS REFERENCE TO RELATED APPLICATIONS

This application claims the benefit of U.S. Provisional Application No. 60/571,303, entitled "Nontoxic Killer of *E. Coli* and Other Problem Microorganisms" filed on May 14, 2004, and U.S. Provisional Application No. 60/573,396, entitled "Nontoxic Killer of *E. Coli* and Other Problem Microorganisms" filed on May 20, 2004, the disclosures of which are incorporated herein by reference in their entirety.

INTRODUCTION

1. Field of the Invention

This invention relates to novel compositions that are useful for eradicating microorganisms from animal carcasses and food preparation surfaces.

2. Background of the Invention

The presence and danger of infection caused by pathologic bacteria, such as *Escherichia*, *Salmonella* and *Listeria*, is an important public health problem in the United States. Annually 500,000 cases of infection and 1,500 deaths are attributed to the problems of these agents in "food processing," especially meats: Health experts estimate that the yearly cost of all food-borne diseases in this country is $5 to $6 billion in direct medical expenses and lost productivity. Infections with the bacteria *Salmonella* alone account for $1 billion yearly in direct and indirect medical costs.

*Salmonella* has been known to cause illness for over 100 years. Every year, approximately 40,000 cases of salmonellosis are reported in the United States. Because many milder cases are not diagnosed or reported, the actual number of infections may be thirty or more times greater. Another common food contaminant, *Escherichia coli* O157:H7, causes an estimated 73,000 cases of infection and 61 deaths in the United States each year (U.S. Centers for Disease Control and Prevention). Processed cattle are the main sources of *E. coli* O157:H7, but other domestic and wild mammals also may harbor these bacteria. Listeriosis, a serious infection caused by eating food contaminated with the bacterium *Listeria monocytogenes*, has recently been recognized as an important public health problem in the United States. In the United States, an estimated 2,500 persons become seriously ill with listeriosis each year; of these, 500 die.

The health conscious public demands food that is safe, sanitary, and free of microorganisms and chemicals. In addition, government health and safety agencies regulate the quality of food. Although the food industry attempts to meet the demands of both the public and the government, large scale food preparing operations inevitably provide environments favorable for the growth of harmful bacteria, fungi, and other microorganisms.

Trends toward shorter cooking times, consumer demand for safety, and willingness to use litigation are increasing the pressure on the food industry to reduce risks in the food chain. Meats are of particular concern because they are easily contaminated with microorganisms and are an ideal environment for growth of bacteria. Pathogens such as *Salmonella*, *Campylobacter*, *Listeria*, *Clostridium*, *Escherichia coli* O157:H7, and the like may be present. When spot-cultures detect any contaminated food products, entire batches are recalled from market. Thus food processors stand to suffer significant financial losses due to inadequate sanitizing methods.

There has been a long felt need for antimicrobial agents which have a high degree of antimicrobial efficacy, and which preferably are safely ingestible by humans while posing no environmental incompatibility. Those antimicrobial agents that are lethal to microorganisms, however, often also are toxic in varying degrees to humans and animals in that both higher and lower forms of life share at least some metabolic pathways. In trying to combat the presence and danger of the bacterial enemy, food processors use many additives, most of which are not effective or are very toxic. Many such chemicals additives (e.g., chlorine bleach) leave residual effects that are unpleasant to the consumer and produce unsafe by-products, for which the processor must search for satisfactory disposal techniques.

In light of the foregoing, there is a need in the art for non-toxic compositions and methods for processing food to reduce microbial growth and for disinfecting food preparation surfaces.

SUMMARY OF THE INVENTION

One embodiment of the present invention provides a concentrated sanitizing solution composition comprising a mixture of benzalkonium chloride, paraben and acetic acid in a ratio of about 1:0.8-1.3:1.6-2.5 (w:w:v), wherein the mixture comprises about 0.2% to about 2.5%.benzalkonium chloride (w/v).

The invention also provides a method of sanitizing an animal carcass comprising contacting the animal carcass with a sanitizing solution, which comprises a mixture of benzalkonium chloride, paraben and acetic acid in a ratio of about 1:0.8-1.3:1.6-2.5 (w:w:v), wherein the concentration of the mixture is microbicidally effective. Preferably, the animal carcass is contacted with the sanitizing solution by immersion or spraying.

Yet another embodiment of the invention provides a method for cleaning hard surfaces in need of disinfection comprising contacting the surface in need of disinfection with a hard surface cleaning composition comprising a benzalkonium chloride, a paraben, and acetic acid in a ratio of 1:0.8-1.3:1.6-2.5 (w:w:v), wherein the hard surface, once disinfected, is essentially free of microbial contamination.

DETAILED DESCRIPTION

Overview

Figure 1:
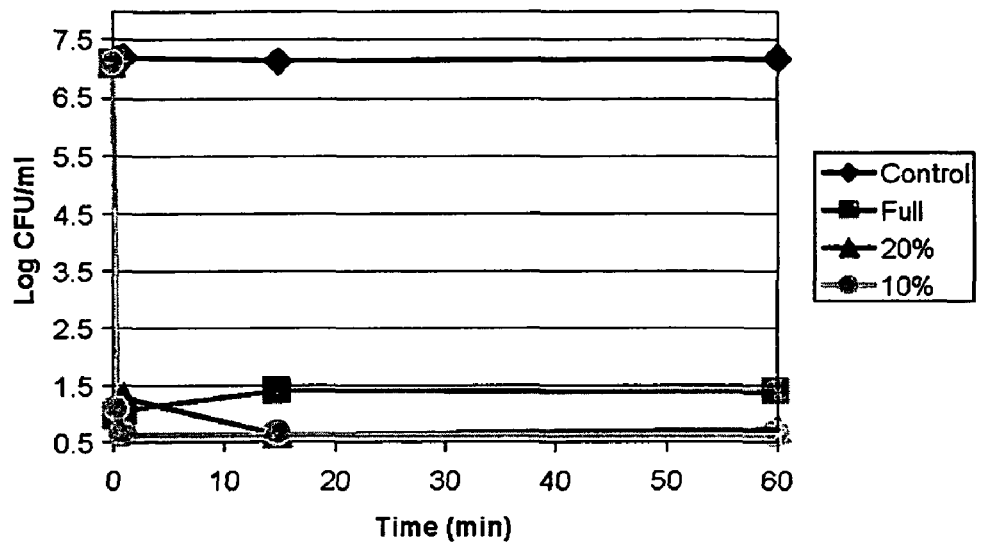
FIG. 1 is a graphical presentation of data showing the killing of *Listeria monocytogenes* by a sanitizing solution of the invention.

The present invention provides novel compositions and methods for controlling enteric pathogens and spoilage organisms such as *Salmonella*, *Escherichia*, *Campylobacter*,

*Listeria, Pseudomonas* and Enterobacteracae on the surface of meat products and food preparation surfaces. The composition of the invention comprises non-toxic low-cost ingredients that effectively kill pathologic bacteria. The composition comprises a solution of acetic acid, paraben and benzalkonium chloride and enough water to dilute the solution to an appropriate microbicidal concentration.

The solution of the invention may be used as a dip or as a spray, or as a combination of these applications. Alternative methods of applying the sanitizing solution to an animal carcass, such as fogging, forming, spreading gelatinous forms of the solution and vacuum treatment, are also contemplated.

Relatively low concentrations of disinfectant compounds are employed, so the invention is economical. In addition, each of the components of the sanitizing solution is a commonly used compound, known to be non-toxic, thus resulting in less environmental impact when disposing of used sanitizing solution.

DEFINITIONS

"Microbicidal" or "bactericidal", as used herein, refers to lethal, irreversible action resulting in complete microbial (or bacterial) cell destruction or incapacitation. On, the other hand, microbistatic or bacteristatic, as used herein, refers to reversible anti-microbial (or anti-bacterial) properties, such that if the organism is rendered free of the agent, the organism can again multiply. Differentiation of antimicrobial "-cidal" or "-static" activity, describe the degree of efficacy. A sanitizer and a disinfectant are, by definition, agents which provide microbicidal activity.

The term "microbicidally effective" or "bactericidally effective" means that treatment results in at least a two $\log_{10}$ reduction and more preferably a three $\log_{10}$ reduction in the resident microbial preparation. A five $\log_{10}$ reduction in 30 seconds is a sanitizing treatment.

The term "essentially-free of microbial contamination," as used herein, means that no microbial contamination can be detected using standard, industry-accepted procedures, such as the AOAC method described below or by swabbing a surface to be tested followed by swiping the same swab across an agar plate and checking for microbial growth.

The term "paraben" refers to a parahydroxybenzoic acid ester. Most preferably, the paraben of the present invention is an alkyl paraben having an alkyl group of from 1-4 carbon atoms, e.g., methyl paraben, ethyl paraben, propyl paraben or butyl paraben.

The term "benzalkonium chloride" refers to an alkyldimethylbenzylammonium chloride of the general formula:

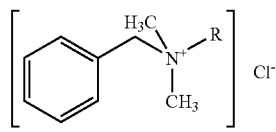

in which R represents an alkyl group of from 8 to 18 carbons. Generally, benzalkonium chloride is available as a mixture of the compounds, wherein R is a C8-18 alkyl. Benzalkonium is also known as parasterol, alkyl benzyl dimethylammonium chloride, or alkyl dimethyl benzylammonium chloride.

The term "alkyl" refers to a monovalent, saturated aliphatic hydrocarbon radical having the indicated number of carbon atoms. For example, a "C1-6 alkyl" or an "alkyl of 1-6 carbons" or "Alk 1-6" would refer to any alkyl group containing one to six carbons in the structure. "C1-20 alkyl" refers to any alkyl group having one to twenty carbons. Alkyl may be a straight chain (i.e. linear) or a branched chain. Lower alkyl refers to an alkyl of 1-6 carbons. Representative examples lower alkyl radicals include methyl, ethyl, n-propyl, n-butyl, n-pentyl, n-hexyl, isopropyl, isobutyl, isopentyl, amyl, sec-butyl, tert-butyl, tert-pentyl and the like. Higher alkyl refers to alkyls of seven carbons and above. These include n-heptyl, n-octyl, n-nonyl, n-decyl, n-dodecyl, n-tetradecyl, n-hexadecyl, n-octadecyl, n-eicosyl, and the like, along with branched variations thereof. The radical may be optionally substituted with substituents at positions that do not significantly interfere with the preparation of compounds falling within the scope of this invention and that do not significantly reduce the efficacy of the compounds. The alkyl may be optionally substituted with one to five substituents independently selected from the group consisting of halo, lower alkoxy, hydroxy, cyano, nitro, or amino.

The word "about" is used to indicate, as is understood in the food processing industry, that some imprecision exists in measurements made by instruments commonly used in the food-processing industry (e.g., scales used to measure weights and containers or flow-measurement devices used to measure volume) and that industry workers, sometimes of relatively low technical skills, are not likely to make measurements as accurately as laboratory workers in the chemical manufacturing industry or in academia. Under these circumstances, "about" preferably indicates a difference between the actual measurement and the intended measurement of no more than 20% when a process measurement actually used is compared to the most accurate measurement available for the type of measurement being made, more preferably a difference of no more than 10%, even more preferably no more than 5%, and most preferably that the difference would fall within two standard deviations from the mean of a (typically commercially available) measuring instrument being used in the process making the measurement, the latter "within-two-standard-deviations" standard typically being a measure of equality. Differences deliberately created by infringers in an attempt to avoid the scope of the claims are also covered by the term "about" as long as the differences remain in the range of equivalents for the invention. All of the preferences as recited above for accidental differences also apply to deliberate differences created by infringers (i.e., a deliberate infringer who is 20% off from a stated range is within a preferred range of equivalents, and so forth). If the word "about" is not present when referring to a measurable quantity, the factors relating to accidental- and deliberate-measurement differences as discussed above are understood to apply.

Other chemical terms are given their standard meaning as understood by one of skill in the art with guidance from standard texts and dictionaries.

Compositions of the Invention

One embodiment of the present invention provides a concentrated sanitizing solution composition (or a solid composition functioning as a precursor to a solution when a solvent, usually water, is later added) comprising a mixture of benzalkonium chloride, paraben and acetic acid in a ratio of 1:0.8-1.3:1.6-2.5 (w:w:v), wherein the concentrated solution is later diluted from about 100-fold to about 10,000-fold prior to use. A preferred aspect of this invention is a concentrated sanitizing solution composition comprising about 0.5% benzalkonium chloride (w/v), 0.5% paraben (w/v), and about 1% acetic acid (v/v), wherein the concentrated solution is diluted from about 100-fold to about 10,000-fold prior to use The invention contemplates a concentrate composition which is diluted to a "use solution" prior to its utilization as a sanitizer. Primarily for reasons of economics of shipping, the concentrate would normally be the form that is marketed and an end user would preferably dilute the concentrate with water or an aqueous diluent to form a use solution. The general constituent concentrations of the sanitizing concentrate formulated in accordance with the invention may be found in Table 1:

TABLE 1

| Constituent | Preferred (%) | More Preferred (%) | Most Preferred (%) |
| --- | --- | --- | --- |
| Benzalkonium chloride (w/v) | e.g. 0.2-2.5 | e.g. 0.3-1.5 | 0.5 |
| Paraben (w/v) | e.g. 0.2-2.5 | e.g. 0.3-1.5 | 0.5 |
| Acetic acid (v/v) | e.g. 0.4-5.0 | e.g. 0.6-3.0 | 1.0 |

As noted previously, it is also possible to provide the concentrate not as a solution but in solid form for ease of shipping, such as a pre-formed mixture of solids or powders or as a freeze-dried remnant of a solution. Commercial efforts are know to be underway to prepare acetic acid in a solid or powdered form that dissolves upon addition of water; the present inventor understands that such solid forms of acetic acid may be available commercially in the near future. Alternatively, acetic acid can be provided as glacial acetic acid or in another concentrated liquid form in a separate container, with the remaining components being provided as solids (their normal purified forms). When acetic acid is provided as a solid, the amount to be used can still be expressed as a volume equivalent and is done so for simplicity in this specification. For example, a preferred ratio of components provides benzalkonium chloride, paraben and acetic acid in a ratio of 1:0.8-1.3:1.6-2.5 (w:w:v) in the form of a concentrate. When a solid composition is provided with acetic acid itself being provided in the form of a solid, enough of the solid form of acetic acid is provided so that the appropriate equivalent volume of acetic acid (1.6-2.5 ml of acetic acid per gram of benzalkonium chloride) is available when the components of the mixture are dissolved.

The other components of the mixture can also be provided as solids in individual containers for increased stability during shipment and/or storage. Alternatively, individual components can be pre-dissolved and provided in the form of concentrated solutions for ease of later mixture and further dilution. When individual components are provided for later mixture and/or dilution, the individual components are generally shipped in a common outer container along with instructions for their proper mixing to form the concentrate composition and/or any of its diluted forms. Provision of instructions that describe preparation of compositions of the invention from commercially available supplies of individual components are considered to be equivalent to provision of the mixtures as described herein.

Although the concentrate or solid precursor mixture is normally intended for use with added water alone in order to simplify preparation of the final use solution by potentially unskilled workers, it is also possible to use other aqueous compositions as a diluting solvent. For example, small amounts of a non-toxic organic solvent (e.g., ethanol) or a salt (e.g., table salt, to provide a desired ionic strength) could be added in an initial dilution to modify solubility of individual components of the mixture or a food-quality dye could be added to distinguish the appearance of the final use solution from other wash solutions used at other stages of the overall process (to avoid processing errors). Preferred aqueous compositions used for diluting from solids or concentrates contain less than 10% non-water components (by weight), more preferably less than 5%, even more preferably less than 2%, and most preferably contain only water (along with any trace components as might be present in a municipal water supply or other source of drinking-quality water).

When dealing with a concentrate composition, the level of active components in a concentrate composition is dependent on the intended dilution factor. Generally, a dilution of about 1 fluid ounce to about 1.0 to about 150.0 gallons of water is used for aqueous antimicrobial sanitizing solutions. The composition shown in the most preferred column of the Table 1 above would be used in a range from about 0.8 fluid ounce per gallon water to about 1.6 fluid ounce per gallon of water.

The invention also provides an animal carcass sanitizing solution composition for treating an animal carcass to eliminate bacteria from the carcass wherein the composition comprises a mixture of benzalkonium chloride, paraben and acetic acid in a ratio of 1:0.8-1.3:1.6-2.5 (w:w:v) in water, wherein the concentration of the mixture in said quantity of water is microbicidally effective. The solution need not be diluted prior to use. The general constituent concentrations of the ready-to-use sanitizing solution formulated in accordance with the invention may be found in Table 2:

TABLE 2

| Constituent | Preferred (%) | More Preferred (%) | Most Preferred (%) |
| --- | --- | --- | --- |
| Benzalkonium chloride (w/v) | 0.00001-0.1 | 0.0002-0.05 | 0.0125-0.025 |
| Paraben (w/v) | 0.00001-0.1 | 0.0002-0.05 | 0.0125-0.025 |
| Acetic acid (v/v) | 0.00002-0.2 | 0.0004-0.1 | 0.025-0.05 |

Immersion Solutions

Poultry processing is similar to the processing of other meat animals. Briefly summarized, caged birds arrive by truck at the processing plant. The birds are hung by their feet on shackles in a dressing line, stunned and bled via throat cuts. After bleeding and while still hung, the birds are scalded, plucked and transferred to an evisceration line, where they are manually or mechanically eviscerated, inspected and spray-washed. Applying present-day practices, the spray may contain chlorine as a disinfecting agent. The last step of the process is chilling in a chill tank, by movement through a counterflow of cold water. The carcasses must reach an internal temperature of 5° C. or below, which usually takes about 45 minutes to one hour in a typical many-thousand gallon tank. After reaching this temperature, the carcasses are packaged or further cut into parts, and refrigerated or frozen. An optional wash of the carcasses or pieces may follow these sanitizing steps. In the practice of the invention, the carcasses or carcass pieces are contacted with disinfectant solution during the initial washing after evisceration, during the chill tank immersion period, or during a spray wash after removal from the chill tank. The disinfectant solution of the invention may also be used in more than one of these processing steps.

For use in chill tank waters, where liquid is being continuously replaced by fresh water, it is necessary to replace the benzalkonium chloride, paraben and acetic acid levels as they are being discarded and reduced through their disinfecting action. Other standard means of dipping carcasses or carcass pieces into solution and monitoring solution ingredients are encompassed by this invention. As tank water levels decrease, more non-toxic sanitizing solution concentrate is added with fresh water to bring the water levels back to operational depth.

The sanitizing solution is preferably agitated to increase the efficacy of the solution and the speed in which the solution kills micro-organisms attached to the meat product. Agitation may be obtained through conventional means including through ultrasonic means, aeration by bubbling air through the solution or by mechanical means, such as strainers, paddles, brushes, or pump driven liquid jets. The sanitizing solution may also be heated to increase the efficacy of the solution in killing micro-organisms.

The immersion composition of the invention may also optionally include any number of adjuvants which add beneficial properties of stability, sequestration, coating and rinsing, etc. These adjuvants may be preformulated with the sanitizing agent of the invention or added to the system simultaneously, or even after, the addition of the sanitizing agent of the invention.

Spray Solutions

Animal carcasses may also be treated by spraying or wiping the solution on the carcasses to be treated. In one embodiment, the solution is sprayed onto the whole animal carcass shortly after killing and evisceration. As discussed above, in poultry, a scalding and defeathering operation occurs before the evisceration.

A preferred mode is a pressure spray with the sanitizing solution of the invention. During application of the spray solution on the meat product, the surface of the meat product may be moved with mechanical action, preferably agitated, rubbed, brushed, etc. Agitation may be by physical scrubbing of the meat product, through the action of the spray solution under pressure or by other means. The agitation increases the efficacy of the spray solution in killing micro-organisms, perhaps due to better exposure of the solution into the crevasses or small colonies containing the micro-organisms. The spray solution, before application, may also be heated to a temperature of about 15 to 20° C., preferably about 20 to 50° C. to increase efficacy. After a sufficient amount of time to kill the micro-organisms on the meat product, the spray solution may be rinsed off the meat product. Alternatively, the sanitizing solution may remain on the surface of the meat product. The continued presence of the sanitizing solution will deter recontamination of the product and prevent mold or slime growth, e.g. during the aging of beef.

Application of the material by spray means may be accomplished using a manual spray wand application, an automatic spray of meat product moving along a production line using multiple spray heads to ensure complete contact or other spray means. One preferred automatic spray application involves the use of a spray booth. The spray booth substantially confines the sprayed composition to within the parameter of the booth. The production line moves the meat product through the entryway into the spray booth in which the meat product is sprayed on all its exterior surfaces with sprays within the booth. After a complete coverage of the material and drainage of the material from the meat product within the booth, the meat product then exits the booth in a fully treated form. The spray booth may comprise steam jets that can be used to apply the antimicrobial compositions of the invention. These steam jets may be used in combination with cooling water to ensure that the treatment reaching the meat product surface is less than 65° C., preferably less than 60° C. The temperature of the spray on the meat product is important to ensure that the meat product is not substantially altered (cooked) by the temperature of the spray.

The spray pattern can be virtually any useful spray pattern. The spray may have a pattern such as a conical spray in which the angle between the perimeter of the spray ranges from less than 180° to about 5°. One preferred spray pattern involves a "fan" spray pattern in which the spray exits the spray head in a substantially planar form and the angle between the extent of the planar spray from edge to edge is about 20° or less, preferably about 15° or less. Other spray patterns can also be useful. The spray also may comprise a fogged material that leaves a fogging apparatus as a dispersion of fog particles in a continuous atmosphere. Such a fogging spray has no defined pattern.

There are a number of parameters which need to be considered if spraying is the application method of choice. The first parameter to determine is the pressure at which the composition is sprayed onto the meat product. While spray pressures as low as about 25 psi (gauge) can be used with some valuable results, a higher spray pressure, greater than about 25, 50, 100, 150 psi and more preferably greater than about 200 psi, are effective in reducing the microbial populations due to the mechanical action of the spray on the meat product surface and on the microbial population remaining on the surface of the meat product. The spray action is best at temperatures less than 65° C. to avoid "cooking" the meat. Further, if increased spray pressures are used, the antimicrobial composition may be applied at lower temperatures, potentially resulting in substantial energy savings. There may be a relationship between application spray duration and antimicrobial efficacy. While spray durations of as little as about 10 seconds may be used, a preferred spray duration is from about 10 to about 30 seconds. Without wishing to be limited to any theory, the increased antimicrobial efficacy resulting from the use of the higher spray pressures is believed to be due to an improvement in penetrating the surface of the meat product, particularly an increased ability to reach into creases and crevices on the surface of the meat product.

For spray application at the end of the processing line of the whole carcass, or for sectioned carcass pieces, the spray solution should contain approximately 0.01 to 0.05% of the concentrated stock solution of the invention. Specific experiments can be run on animal carcasses during typical in-plant operations, using formulations representing different concentration ranges and pH's in order to establish optimum effectiveness without excess usage of disinfecting chemicals.

The sanitizing solution may also include any number of constituents such as various organic compounds which facilitate the functions provided above. Organic solvents which have been found useful include simple alkyl alcohols such as ethanol, isopropanol, n-propanol, and the like. Polyols are also useful additives in accordance with the invention, including propylene glycol, polyethylene glycol, glycerol, sorbitol, and the like. Any of these compounds may be used singly or in combination with other organic or inorganic constituents or, in combination with water or in mixtures thereof. Preferably, the solvent consists of from about 1% to about 60% of an organic solvent.

Generally, the carrier makes up a large portion of the composition of the invention and may essentially be the balance of the composition apart from the active antimicrobial composition adjuvants, and the like. Here again, the carrier concentration and type will depend upon the nature of the composition as a whole, the environmental storage and method of application including concentration of the antimicrobial agent, among other factors. Notably the carrier should be chosen and used at a concentration which does not inhibit the antimicrobial efficacy of the act in the composition of the invention.

When the solution is to be sprayed on a carcass, a thickener such as a polysaccharide may be added to the solution such that the spray solution sticks or holds onto the treated carcass. Thickeners useful in the present invention are those which do not leave contaminating residue on the surface of application, i.e., constituents which are incompatible with food or other sensitive products in contact areas. Generally, thickeners that may be used in the present invention include natural gums such as xanthan gum. Also useful in the present invention are cellulosic polymers, such as carboxymethyl cellulose. Generally, the concentration of thickener use in the present invention will be dictated by the desired viscosity within the final composition. However, as a general guideline, concentration of thickener within the present composition ranges from about 0.1 wt-% to about 1.5 wt-%, preferably from about 0.1 wt-% to about 1.0 wt-%, and most preferably from about 0.1 wt-% to about 0.5 wt-%.

The spray composition of the invention may also optionally include any number of adjuvants which add beneficial properties of stability, sequestration, sheeting and rinsing, etc. These adjuvants may be preformulated with the sanitizing agent of the invention or added to the system simultaneously, or even after, the addition of the sanitizing agent of the invention.

Disinfection of Surfaces

The hard surface cleaning compositions of the present invention comprise benzalkonium chloride, paraben and acetic acid in a ratio of about 1:0.8-1.3:1.6-2.5, wherein the concentration of the mixture is microbicidally effective.

In addition to the above-mentioned required materials, other adjunct ingredients can also be included in compositions of the present invention, at their conventional art-established levels for use (generally, adjunct materials comprise, in total, from about 30% to about 99.9%, preferably from about 70% to about 95%, by weight of the compositions). Examples of adjunct ingredients are buffers, builders, chelants, filler salts, dispersants, enzymes, enzyme boosters, perfumes, thickeners, clays, solvents, and mixtures thereof. This list is not meant to be totally inclusive or exclusive of materials that are compatible for use in the present invention.

Water is typically used as a filler solvent for "spray on" or "light duty" compositions or to make up the balance of concentrates. The compositions of the present invention, other than concentrates wherein the consumer adds the carrier prior to use, comprise at least 40%, preferably, at least 45%, more preferably at least 50% by weight, of water as carrier. Concentrates prepared according to the present invention are diluted prior to use to the aforementioned concentrations.

The present invention also provides a method for cleaning hard surfaces in need of disinfection wherein the hard surface, once cleaned, is essentially free of microbial contamination. The present method comprises the step of contacting the surface in need of cleaning with a hard surface cleaning composition described herein. The method may comprise using the cleaning composition directly (neat) or first diluting the composition in a sufficient amount of water or other carrier.

EXAMPLES

The following examples are given to provide representative compositions and methods included as part of this invention. Throughout the examples chemical formulas will be used to name compounds (e.g. $NaHCO_3$ is sodium bicarbonate) as appropriate.

Example 1

Preparation of Stock Solution

A concentrated stock solution was prepared by adding 0.5 g benzalkonium chloride, 0.5 g paraben, and 1 ml of glacial acetic acid to 100 ml water. The mixture was stirred at room temperature until dissolved. The solution was stored at room temperature. The solution is stable for one year when properly stored, preferably in a dry, cool (<100° F.) location.

Example 2

Inhibition of E. coli Growth on Agar Plates $10^8$ cells of Escherichia coli were spread on a plate and then were exposed to 1.0 ml of a 0.05% or 0.025% dilution of the stock solution of Example 1 for one hour at room temperature. The sanitizing solution is absorbed into the growth media. The cells were then washed in PBS and serially diluted. The diluted cells were spread onto LB agar plates and then incubated overnight at 37° C.

The plates were then examined and the number of bacterial colonies were counted. All experiments were done in duplicate. The results of this examination are shown in Table 1. No viable E. coli remained following exposure to either dilution of the non-toxic solution of the invention after an one hour exposure at room temperature.

TABLE 1

| | Number of colonies | | | | | | |
|---|---|---|---|---|---|---|---|
| | Undiluted | $10^1$-fold | $10^2$-fold | $10^3$-fold | $10^4$-fold | $10^5$-fold | $10^6$-fold |
| Control | lawn | lawn | lawn | lawn | n.d. | tntc | 186 |
| Control | lawn | lawn | lawn | lawn | n.d. | tntc | 260 |
| 0.05% solution | 0 | 0 | 0 | 0 | 0 | n.d. | n.d. |
| 0.05% solution | 0 | 0 | 0 | 0 | 0 | n.d. | n.d. |
| 0.025% solution | 0 | 0 | 0 | 0 | 0 | n.d. | n.d. |
| 0.025% solution | 0 | 0 | 0 | 0 | 0 | n.d. | n.d. | n.d. = not determined
tntc = too numerous to count

Example 3

Inhibition of Salmonella enteriditis Growth on Agar Plates $10^8$ cells of Salmonella enteriditis in 0.1 ml of media were exposed to 1.0 ml of a 0.05% or 0.025% dilution of the stock solution of Example 1 for one hour at room temperature. The cells were then washed in PBS, by centrifugation and re-suspension in the same volume, and then serially diluted. The diluted cells were spread onto LB agar plates and then incubated overnight at 37° C. The "control cells" were diluted in media, incubated for one hour without addition of the sanitizing solution, and then washed and plated in a manner similar to that for the treated cells.

The plates were then examined and the number of bacterial colonies were counted. All experiments were done in duplicate. The results of this examination are shown in Table 2. No viable Salmonella remained following exposure to either dilution of the non-toxic solution of the invention after an one hour exposure at room temperature.

TABLE 2

| | Undiluted | $10^1$-fold | $10^2$-fold | $10^3$-fold | $10^4$-fold | $10^5$-fold | $10^6$-fold |
|---|---|---|---|---|---|---|---|
| Control | lawn | lawn | lawn | lawn | n.d. | tntc | 540 |
| Control | lawn | lawn | lawn | lawn | n.d. | tntc | 400 |
| 0.05% solution | 0 | 0 | 0 | 0 | 0 | n.d. | n.d. |
| 0.05% solution | 0 | 0 | 0 | 0 | 0 | n.d. | n.d. |
| 0.025% solution | 0 | 0 | 0 | 0 | 0 | n.d. | n.d. |
| 0.025% solution | 0 | 0 | 0 | 0 | 0 | n.d. | n.d. | n.d. = not determined
tntc = too numerous to count

Example 4

$10^8$ cells of *Salmonella enteriditis* or *E. coli* in 0.1 ml of media were exposed to 1.0 ml of a 0.01% or 0.125% dilution of the stock solution of Example 1 for one hour at room temperature. The cells were then washed in PBS and serially diluted. The diluted cells were spread onto LB agar plates and then incubated overnight at 37° C. The "control cells" were diluted in media, incubated for one hour without addition of the sanitizing solution, and then washed and plated in a manner similar to that for the treated cells.

The plates were then examined and the number of bacterial colonies were counted. All experiments were done in duplicate. The results of this examination are shown in Table 3. No viable bacterial cells remained following exposure to either dilution of the non-toxic solution of the invention after an one hour exposure at room temperature.

TABLE 3

| Dilution (%) | Bacteria | Colonies pre-exposure | Colonies post-exposure | % Kill |
|---|---|---|---|---|
| 0.1 | *E. coli* | 400 | 0 | 100 |
| 0.1 | *Salmonella* | 500 | 0 | 100 |
| 0.125 | *E. coli* | 400 | 0 | 100 |
| 0.125 | *Salmonella* | 500 | 0 | 100 |

Example 5

Sterile Water Testing of *E. coli*

A solution was prepared at the concentration of 0.025% of the concentrated stock solution of Example 1 in water containing: 0 parts per million (ppm) $CaCO_3$, 550 ppm $CaCO_3$, or 900 ppm $CaCO_3$. In addition, control samples consisting just of water containing 0 ppm $CaCO_3$, 550 ppm $CaCO_3$, and 900 ppm $CaCO_3$, respectively, were used as controls. A population of *E. coli* cells were stirred into each of the test and control solutions. Each resulting cell-solution mixture was sampled at 30 and 60 seconds. No viable *E. coli* cells were detected after 30 or 60 seconds.

The AOAC (Association of Official Analytical Chemists) method requires 99.999% reduction the number of cells within 30 seconds. The 60 second interval is used to determine trends in case of failure. Each of the tested samples showed 100% reduction in *E. coli*.

Example 6

Available Chlorine Testing of *Staphylococcus aureus*

A solution was prepared at the concentration of 0.025% of the stock solution of Example 1 in water containing: 0 parts per million (ppm) $CaCO_3$, 550 ppm $CaCO_3$, or 900 ppm $CaCO_3$. In addition, control samples consisting just of water containing 50 ppm, 100 ppm, and 220 ppm free chlorine, respectively, were prepared. 50 µl of a 24-hour culture of *S. aureus* was stirred into each of the test and the chlorine solutions. Each resulting cell-solution mixture was sampled at 30 and 60 seconds. An additional 50 µl of the *S. aureus* culture was added to each solution and the solution sampled at 30 and 60 seconds post-addition. This process was repeated until a total of 500 µl of the *S. aureus* culture had been added to each preparation, over a 15 minute period.

In order to pass the assay, the non-toxic solution of the invention must kill *S. aureus* at a rate greater than or equal to that of the 100 ppm free chlorine solution. All samples containing the non-toxic solution of the invention showed no growth after each addition of *S. aureus*.

Example 7

Animal Toxicity Testing

The sanitizing compositions of the invention are tested for contact and ingestion toxicity in both laboratory animals and human. A patch of skin on laboratory mice is shaved and a pad saturated with the concentrated solution of Example 1 is placed against the skin. No skin irritation is detected. A diluted (aqueous) sanitizing solution of the invention is used to replace the drinking water of laboratory mice for several days. No adverse effects are seen. Human test for skin irritation and ingestion toxicity, similarly, show no significant toxicity of the sanitizing solution of the invention.

Example 8

Preliminary Results of the Effect of Non-Toxic Sanitizer Solution on Two Microorganisms, *Listeria monocytogenes* and *E. coli* O157:H7

Solutions were prepared in accordance with the invention as described and were tested for ability to kill microorganisms. In this example, the concentrated non-toxic sanitizer solution was prepared by adding together 0.5 g benzalkonium chloride, 0.5 g methylparaben, and 1.0 ml glacial acetic acid, followed by diluting to 100 ml with water.

In the first preliminary test using *Listeria monocytogenes*, solutions were as follows:
Control—No sanitizer
Full—Concentrated non-toxic sanitizer solution
20%—1:5 dilution of non-toxic sanitizer solution
10%—1:10 dilution of non-toxic sanitizer solution Initial count of *Listeria monocytogenes* was approximately $1 \times 10^7$ cells/ml. Five strains were used together: Scott A, 103, 108, 101 and 310. Exposure times: 0, 15 sec, 30 sec, 15 min and 60 min. Data points are averages of replicate tests and duplicate plates. Results of the tests are shown graphically in FIG. 1.

Conclusion: Non-toxic solution at as low as 10% killed over 6 logs of *L. monocytogenes* a cells in 15 sec., and no increase in cell count was noted over a period of 1 hour.

Figure 2:
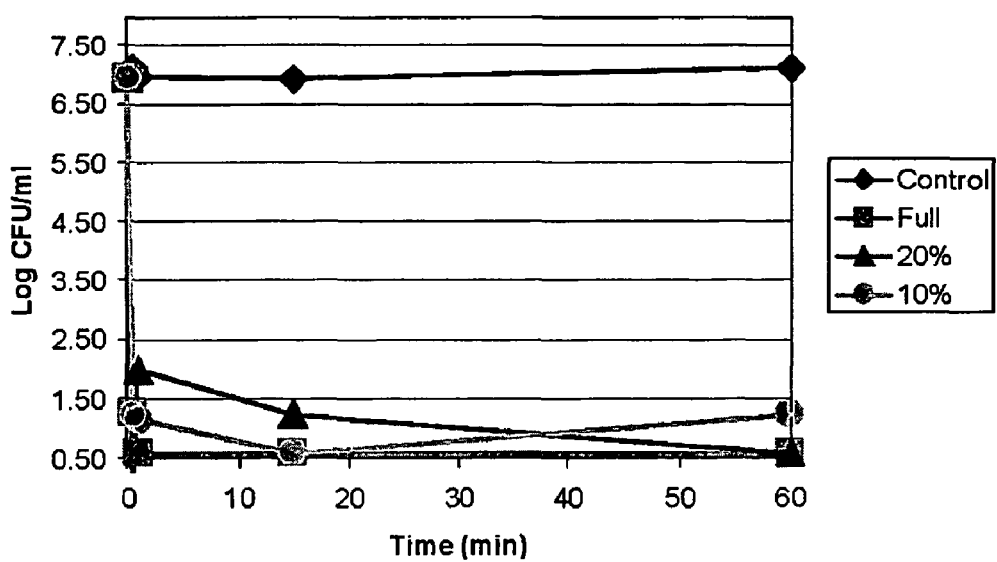
FIG. 2 is a graphical presentation of data showing the killing of *Escherichia coli* by a sanitizing solution of the invention.

In the second preliminary test using *Escherichia coli* O157: H, solutions were as follows:
Control—No sanitizer
Full—Concentrated non-toxic sanitizer solution
20%—1:5 dilution of non-toxic sanitizer solution
10%—1:10 dilution of non-toxic sanitizer solution Initial count of *Escherichia coli* O157:H7 was approximately $1\times10^7$ cells/ml. Five strains were used together. Exposure times: 0, 15 sec, 30 sec, 15 min and 60 min. Data points are averages of replicate tests and duplicate plates. Results of the tests are shown graphically in FIG. 2.

Conclusion: Non-toxic solution at as low as 10% killed over 6 logs of *E. coli* O157:H7 cells in 15 sec and no significant increase in cell count was noted over a period of 1 hour.

Example 9

Results of the Effect of Low Concentrations of Non-Toxic Solution on *Listeria monocytogenes*, *Salmonella Typhimurium* and *E. coli* O157:H7

Figure 3:
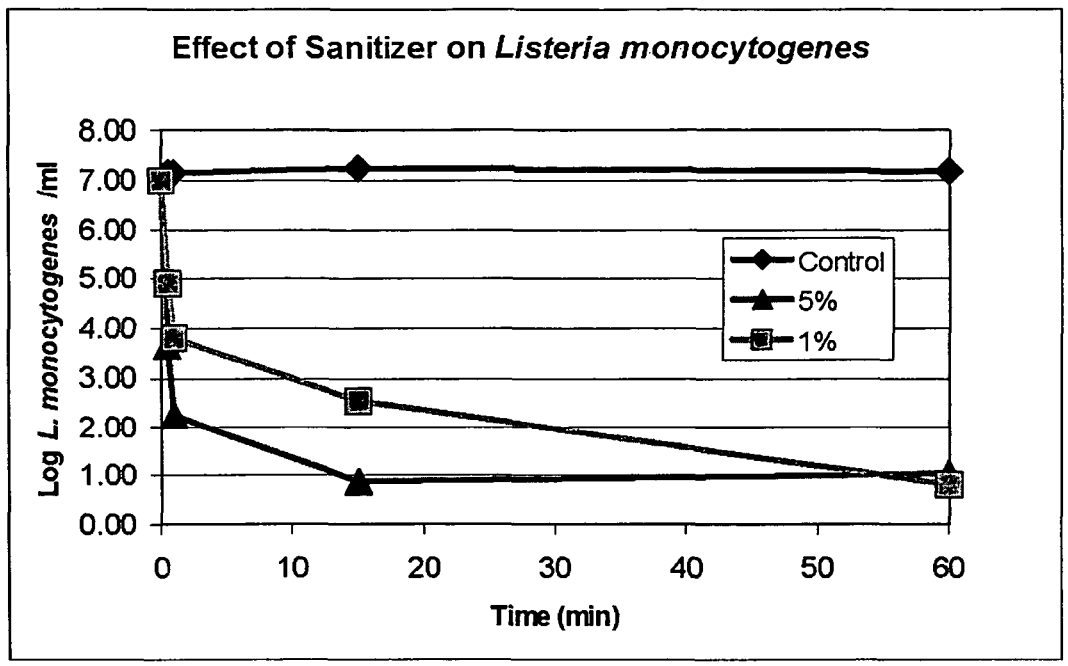
FIG. 3 is a graphical presentation of data showing the killing of *Listeria monocytogenes* by a sanitizing solution of the invention.
Figure 4:
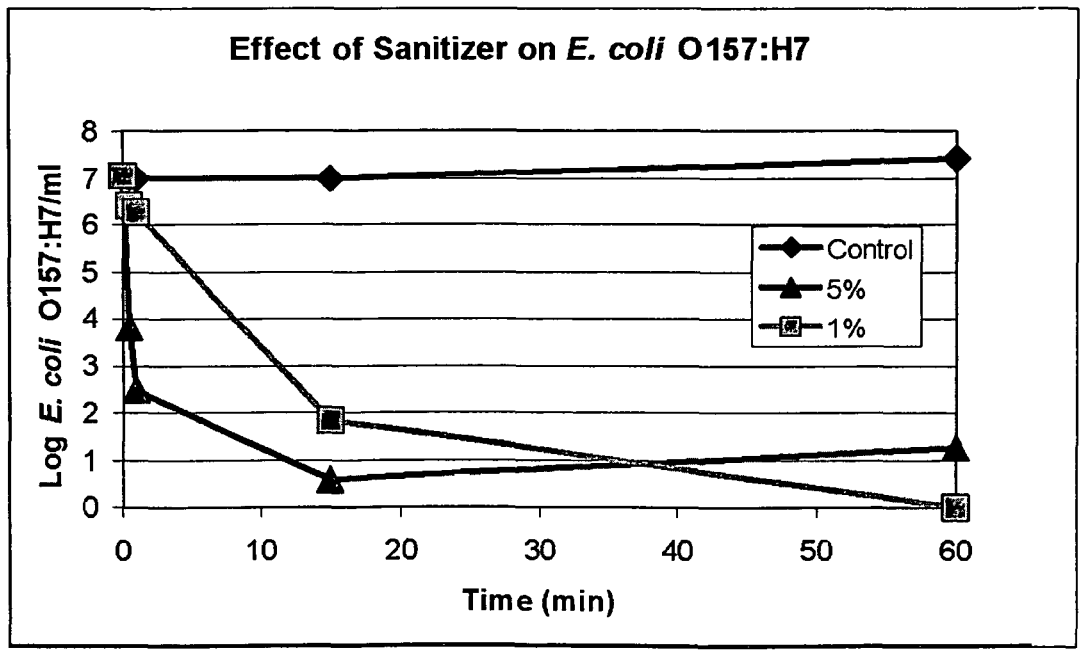
FIG. 4 is a graphical presentation of data showing the killing of *Escherichia coli* by a sanitizing solution of the invention.
Figure 5:
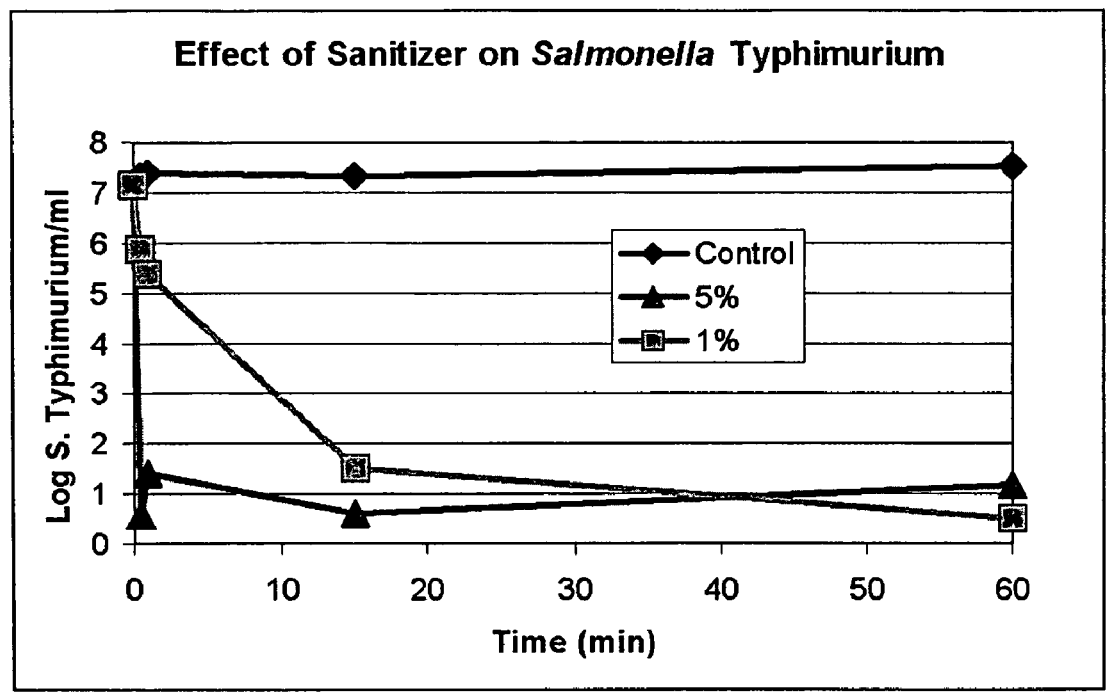
FIG. 5 is a graphical presentation of data showing the killing of *Salmonella Typhimurium* by a sanitizing solution of the invention.

Additional testing of solutions of the invention, with the concentrated starting solution of non-toxic sanitizing solution being prepared as in Example 8, were carried out.
Holding Solution Solution of Phosphate buffer plus appropriate amount of sanitizer compound were prepared to attain listed concentrations; viable cells were inoculated into this composition and held for varying lengths of time to determine sanitizer antimicrobial effectiveness. The holding solution had a pH in the range from 2.5 to 4, depending on the concentration of the sanitizing solution being tested.
Neutralizer Buffer One ml of the holding solution was transferred to 9 ml of neutralizer buffer in order to stop the sanitizer's reaction with the test microorganism. Also, the transfer of 1 ml to 9 ml created a one log dilution for the purposes of enumeration of survivors. After mixing, the neutralizing buffer had a pH in the range from 4 to 7, depending on the concentration of the sanitizing solution being tested.
Phosphate Buffer One ml of the neutralizer buffer reaction tube was transferred to 99 ml of phosphate buffer, creating a 2 log dilution of surviving cells from the neutralizer buffer. In all, cells were diluted 3 logs from the holding solution for enumeration purposes. After mixing, the phosphate buffer had a pH in the range from 5 to 7, depending on the concentration of the sanitizing solution being tested.
First Organism Test
Control B—No sanitizer
5%—1:20 dilution of non-toxic sanitizing solution
1%—1:100 dilution of non-toxic sanitizing solution Initial count of *Listeria monocytogenes* was approximately $1\times10^7$ cells/ml. Five strains were used together. Exposure times: 0, 15 sec, 30 sec, 15 min and 60 min. Data points are averages of replicate tests and duplicate plates. Results are shown graphically in FIG. 3.
Conclusion:
Non-toxic solution at 1% killed:
Approximately 3.5 logs (>99.9%) of *L. monocytogenes* cells in 30 seconds
Approximately 4.5 logs (>99.99%) of *L. monocytogenes* cells in 15 min
Approximately 6 logs (99.9999%) of *L. monocytogenes* cells in 60 min
Non-toxic solution at 5% killed:
Approximately 5 logs (99.999%) of *L. monocytogenes* cells in 30 sec
Approximately 6 logs (99.9999%) of *L. monocytogenes* cells in 15 min
Second Organism Test
Control B—No sanitizer
5%—1:20 dilution of non-toxic solution
1%—1:100 dilution of non-toxic solution Initial count of *Escherichia coli* O157:H7 was approximately $1\times10^7$ cells/ml. Five strains were used together. Exposure times: 0, 15 sec, 30 sec, 15 min and 60 min. Data points are averages of replicate tests and duplicate plates. Results are shown graphically in FIG. 4.
Conclusion:
Non-toxic solution at 1% killed:
Approximately 5 logs (99.999%) of *E. coli* O157:H7 in 15 min
Approximately 6 logs (99.9999%) of *E. coli* O157:H7 cells in 60 min
Non-toxic solution at 5% killed:
Approximately 3.5 logs (>99.9%) of *E. coli* O157:H7 cells in 30 sec
Approximately 4.5 logs (>99.99%) of *E. coli* O157:H7 cells in 15 min
Approximately 6 logs (99.9999%) of *E. coli* O157:H7 cells in 60 min
Third Organism Test
Control B—No sanitizer
5%—1:20 dilution of non-toxic solution
1%—1:100 dilution of non-toxic solution Initial count of *Salmonella Typhimurium* was approximately $1\times107$ cells/ml. Five strains were used together. Exposure times: 0, 15 sec, 30 sec, 15 min and 60 min. Data points are averages of replicate tests and duplicate plates. Results are shown graphically in FIG. 5.
Conclusion:
Non-toxic solution at 1% killed:
Approximately 5.5 logs (>99.999%) of *Salmonella Typhimurium* in 15 min
Approximately 6 logs (99.9999%) of *Salmonella Typhimurium* cells in 60 min
Non-toxic solution at 5% killed:
Approximately 6 logs (99.9999%) of *Salmonella Typhimurium* cells in 15 sec

I claim:

1. A concentrated sanitizing composition consisting of a mixture of benzalkonium chloride, paraben and acetic acid in a ratio of about 1:0.8-1.3:1.6-2.5 (w:w:v), wherein said benzalkonium chloride is present in an amount of about 0.2% to about 2.5% (w/v), and optionally any number of safely ingestible adjuvants selected from the group consisting of food quality-dyes, salts, thickeners, polyols, solvents and cellulosic polymers.

2. The concentrated sanitizing composition of claim 1, wherein the amount of said benzalkonium chloride is about 0.3% to about 1.5% (w/v).

3. The concentrated sanitizing composition of claim 2, wherein the amount of said benzalkonium chloride is about 0.4% to about 0.6% (w/v).

4. The concentrated sanitizing composition of claim 1, wherein the mixture is an aqueous solution.

5. The concentrated sanitizing composition of claim 1, wherein the paraben is selected from the group consisting of alkyl parabens having an alkyl group of from 1 to 4 carbon atoms.

6. The concentrated sanitizing composition of claim 1, wherein the benzalkonium chloride is a mixture of alkyldimethylbenzylammonium chlorides of the general formula:

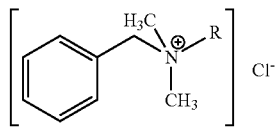

in which R represents a mixture of alkyls from $C_8H_{17}$ to $C_{18}H_{37}$.

7. A sanitizing composition consisting of: (a) a quantity of water; and (b) a mixture of benzalkonium chloride, paraben and acetic acid in a ratio of 1:0.8-1.3:1.6-2.5 (w:w:v), wherein the concentration of the mixture in said quantity of water is microbicidally effective, and optionally any number of safely ingestible adjuvants selected from the group consisting of food quality-dyes, salts, thickeners, polyols, solvents and cellulosic polymers.

8. The sanitizing composition of claim 7, wherein the concentration of the benzalkonium chloride is between 0.00001% (w/v) and 0.1% (w/v).

9. The sanitizing composition of claim 8, wherein the concentration of the benzalkonium chloride is between 0.0002% (w/v) and 0.05% (w/v).

10. The sanitizing composition of claim 9, wherein the concentration of the benzalkonium chloride is between 0.0125% (w/v) and 0.025% (w/v).

11. The sanitizing composition of claim 7, wherein the paraben is selected from the group consisting of alkyl parabens having an alkyl group of from 1-4 carbon atoms.

12. The sanitizing composition of claim 7, wherein the benzalkonium chloride is a mixture of alkyldimethylbenzylammonium chlorides of the general formula:

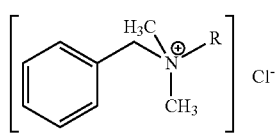

in which R represents a mixture of alkyls from $C_8H_{17}$ to $C_{18}H_{37}$.

13. A method of sanitizing an animal carcass comprising:
a) contacting said animal carcass with the sanitizing solution of claim 7.

14. The method of claim 13, wherein the concentration of the benzalkonium chloride is between 0.00001% (w/v) and 0.1% (w/v).

15. The method of claim 14, wherein the concentration of the benzalkonium chloride is between 0.0002% (w/v) and 0.05% (w/v).

16. The method of claim 15, wherein the concentration of the benzalkonium chloride is between 0.0125% (w/v) and 0.025% (w/v).

17. The method of claim 13, wherein the paraben is selected from the group consisting of alkyl parabens having an alkyl group of from 1-4 carbon atoms.

18. The method of claim 13, wherein the benzalkonium chloride is a mixture of alkyldimethylbenzylammonium chlorides of the general formula:

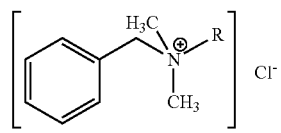

in which R represents a mixture of alkyls from $C_8H_{17}$ to $C_{18}H_{37}$.

19. The method of claim 13, wherein contacting the animal carcass with the sanitizing solution comprises immersing the animal carcass in the sanitizing solution and subsequently removing the animal carcass from the sanitizing solution.

20. The method of claim 19, further comprising the step of rinsing the sanitizing solution from the animal carcass after removing the animal carcass from the sanitizing solution.

21. The method of claim 19, wherein the animal carcass is contacted with sanitizing solution during the initial washing after evisceration.

22. The method of claim 19, wherein the animal carcass is contacted with sanitizing solution during a chill tank immersion period.

23. The method of claim 19, wherein the animal carcass is contacted with sanitizing solution during after removal from a chill tank.

24. The method of claim 13, wherein contacting the animal carcass with the sanitizing solution comprises spraying the animal carcass with the sanitizing solution.

25. The method of claim 24, further comprising the steps of: allowing the sanitizing solution to remain in contact with the animal carcass for 5 to 60 minutes; and rinsing the sanitizing solution from the animal carcass.

26. The method of claim 24, wherein said adjuvant is present and is a thickener.

27. A method for cleaning hard surfaces in need of disinfection comprising: the step of contacting the surface in need of disinfection with said sanitizing solution of claim 7, wherein the hard surface, once disinfected, is essentially free of microbial contamination.

28. The method of claim 27, wherein the concentration of the benzalkonium chloride is between 0.00001% (w/v) and 0.1% (w/v).

29. The method of claim 28, wherein the concentration of the benzalkonium chloride is between 0.0002% (w/v) and 0.05% (w/v).

30. The method of claim 29, wherein the concentration of the benzalkonium chloride is between 0.0125% (w/v) and 0.025% (w/v).

31. The method of claim 27, wherein the paraben is selected from the group consisting of alkyl parabens having an alkyl group of from 1-4 carbon atoms.

32. The method of claim 27, wherein the benzalkonium chloride is a mixture of alkyldimethylbenzylammonium chlorides of the general formula:

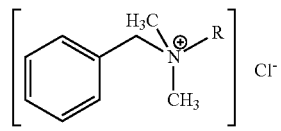

in which R represents a mixture of alkyls from $C_8H_{17}$ to $C_{18}H_{37}$.

33. The sanitizing composition of claim 1, wherein if said composition is in fully solid form, sufficient acetic acid in its solid form is present to provide a weight:volume ratio of 1 gram of benzalkonium chloride to 1.6-2.5 milliliter acetic acid ratio when liquefied upon dilution with an aqueous solvent.

34. A sanitizing composition consisting of benzalkonium chloride, paraben and acetic acid in amounts sufficient to provide a ratio of about 1:0.8-1.3:1.6-2.5 (w:w:v) when mixed to form a mixture, and optionally any number of safely ingestible adjuvants selected from the group consisting of food quality-dyes, salts, thickeners, polyols, solvents and cellulosic polymers, wherein (1) each recited component of said mixture is present in a separate container located inside a common container or (2) two or more components are present in a first container and at least one other component is present in a second container, said first and second containers being located in a common container.

35. The concentrated sanitizing composition of claim 1, wherein said polyols is/are selected from the group consisting of propylene glycol, polyethylene glycol, glycerol and sorbitol.

36. The concentrated sanitizing composition of claim 1, wherein said thickener is selected from the group consisting of polysaccharide and natural gums.

37. The concentrated sanitizing composition of claim 1, wherein said solvent is selected from the group consisting of water or ethanol.

38. The concentrated sanitizing composition of claim 1, wherein said cellulosic polymer is carboxymethyl cellulose.

39. The sanitizing composition of claim 7, wherein said polyols is/are selected from the group consisting of propylene glycol, polyethylene glycol, glycerol and sorbitol.

40. The sanitizing composition of claim 7, wherein said thickener is selected from the group consisting of polysaccharide and natural gums.

41. The sanitizing composition of claim 7, wherein said solvent is ethanol.

42. The sanitizing composition of claim 7, wherein said cellulosic polymer is carboxymethyl cellulose.

43. The concentrated sanitizing composition of claim 1, consisting of a mixture of benzalkonium chloride, paraben and acetic acid.

44. The concentrated sanitizing composition of claim 1, consisting of a mixture of water, benzalkonium chloride, paraben and acetic acid.

45. The sanitizing composition of claim 7, consisting of a mixture of water, benzalkonium chloride, paraben and acetic acid.

46. A method of rinsing food comprising: a) contacting said food with the sanitizing solution of claim 7.

* * * * *